Figure 1:
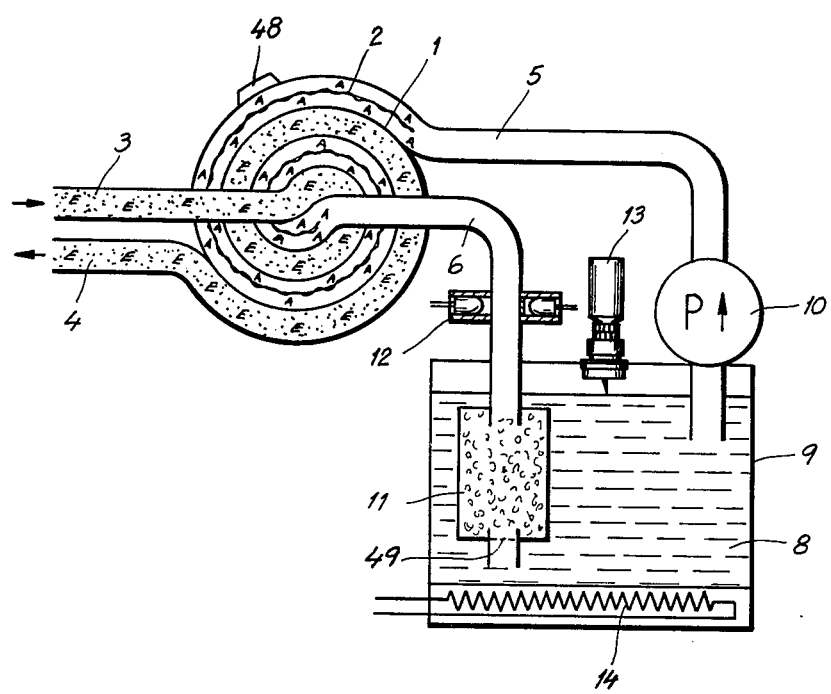

United States Patent [19]
Hyden

[11] 4,192,748
[45] Mar. 11, 1980

[54] DIALYSIS APPARATUS WITH SELECTIVE CHEMICAL ACTIVITY

[76] Inventor: Viktor H. Hyden, Geijersgatan 6, 411 34 Goteburg, Sweden

[21] Appl. No.: 738,328

[22] Filed: Nov. 2, 1976

Related U.S. Application Data

[63] Continuation of Ser. No. 480,811, Jun. 19, 1974, abandoned.

[30] Foreign Application Priority Data

Jul. 5, 1973 [SE] Sweden .............................. 7309501

[51] Int. Cl.$^2$ .............................................. B01D 31/00
[52] U.S. Cl. ..................................... 210/87; 210/96.2; 210/258; 210/259; 210/321 B
[58] Field of Search ...................... 210/22, 321 B, 494, 210/19, 87, 96 M, 259, 255, 258; 195/68

[56] References Cited

U.S. PATENT DOCUMENTS

| | | | |
|---|---|---|---|
| 3,503,877 | 3/1970 | Berry | 210/19 |
| 3,522,346 | 7/1970 | Chang | 210/22 X |
| 3,579,441 | 5/1971 | Brown | 210/321 B X |
| 3,608,729 | 9/1971 | Haselden | 210/321 B |
| 3,619,423 | 11/1971 | Galletti et al. | 210/321 B X |
| 3,645,852 | 2/1972 | Axen et al. | 195/68 |
| 3,703,959 | 11/1972 | Raymond | 210/321 B X |
| 3,880,760 | 4/1975 | Flanouli | 210/494 M X |
| 3,888,250 | 6/1975 | Hill | 210/DIG. 23 X |
| 4,061,141 | 12/1977 | Hydeh et al. | 128/214 R |

*Primary Examiner*—Frank A. Spear, Jr.
*Attorney, Agent, or Firm*—Sherman & Shalloway

[57] ABSTRACT

A compact dialysis unit having a dialysis membrane forming a partition between a liquid to be dialyzed and a dialysate, at least that surface of the membrane facing the liquid to be dialyzed having a selectively chemically active therapeutic substance fixed thereon and a selectively acting adsorbent in the dialysate circuit. Preferably, the dialysate circuit includes at least one dosimeter and a safety warning system.

10 Claims, 12 Drawing Figures

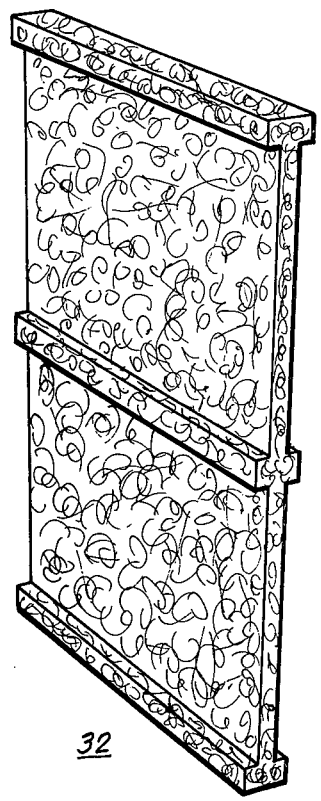
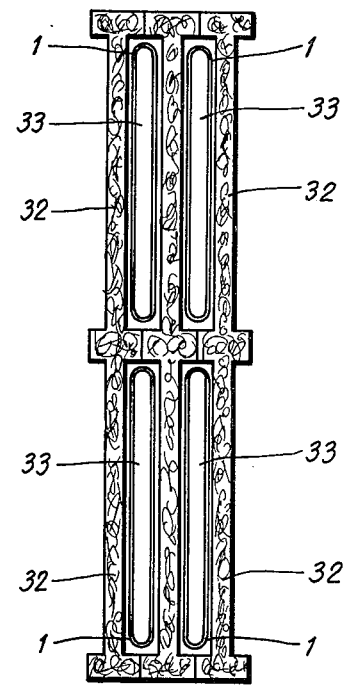
Fig. 7    Fig. 8
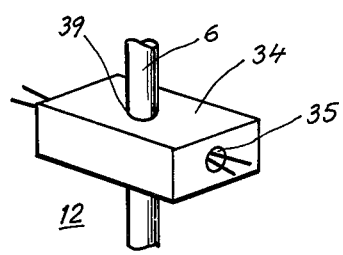
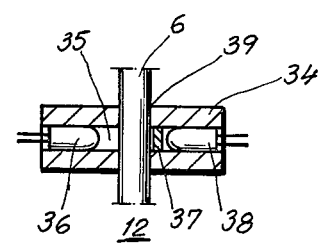
Fig. 9    Fig. 10

DIALYSIS APPARATUS WITH SELECTIVE CHEMICAL ACTIVITY

This is a continuation, of application Ser. No. 480,811 filed June 19, 1974, now abandoned.

The present invention relates to devices for dialysis, preferably, as applied to hemodialysis. However, the devices can also be used for purification of liquids other than blood. According to the present invention, enzymes, antibiotics or substances with a similar chemical character are insolubilized on the dialysis membrane of the apparatus which thereby is rendered selectively chemically active and results in improved and faster dialysis. Furthermore, the apparatus according to the present invention can be utilized for chemotherapy in such pathological conditions, which can be treated by selectively affecting the liquid phase of the blood, and blood cells, for example, by enzymatic degradation. The apparatus according to the present invention operates with recirculating dialysate, which is continuously purified by means of an adsorbent, preferably, one which is preconditioned zirconium phosphate and/or zirconium oxide, and provided with at least one drop dosimeter for supplying to the dialysate the blood constituents desired. The blood constituents can pass through the pores of the dialysis membrane which preferably are of a size substantially greater than the pores of conventional dialysis membranes. A spectrometer with a filter adjusted to hemoglobin is connected into the circuit of the dialysate and alarms via an electronic circuit for use when blood or free hemoglobin appears in the dialysate. Those parts of the device which directly or indirectly come into contact with blood and the absorbent are preferably intended to be disposable.

A preferred embodiment of the present invention consists of an artificial kidney with the possibility of chemotherapy, said artificial kidney having very small dimensions, high capacity and being simple and inexpensive to manufacture and utilize and, therefore, also being well suited for home dialysis. The artificial kidney is designed as a compact unit having a weight of 5-7 kg, inclusive of the dialysate, and need be connected only to a conventional source of current supply.

In the following, dialysis devices are described, portions of which are previously known and, with the apparatus according to the present invention, emphasis being laid on the so-called artificial kidneys. However, it should also be noted that the apparatus according to the present invention, like several known dialysis apparatuses, can also be used for purification of liquids other than blood.

It has been known for a relatively long time to treat patients suffering from an acutely or chronically failing kidney function with an artificial kidney, which during the healing period or while waiting for a suitable kidney transplant performs the function of the natural kidney to eliminate urea and other undesirable constituents in the blood. The patient's blood can flow from an artery through the artificial kidney and return to a vein by means of an extracorporeal shunt arranged for this purpose. The original design of the artificial kidney, of which a plurality of improved variants are still predominantly in use at hemodialysis, is a dialysis apparatus with a semipermeable membrane, which separates a blood stream and a dialysate stream, in such a manner that undesirable as well as some desirable substances in the blood pass through the pores of the dialysis membrane to the dialysate. This is a purely physical method without any kind of chemical activity. The original devices of this type were very large and heavy units, which contained up to 1000 liters of dialysate and were both expensive and labourdemanding. Therefore, only a limited number of dialysis centers could be established in special clinics. Owing to successive improvements of the original types of devices, including e.g. improved dialysis membrane, pre-fabricated sterile disposable membrane packs, compact design, improved instrumentation etc., dialysis apparatuses have been developed which today have much smaller dimensions and show better dialysis results and which, furthermore, involve lower initial and operational costs. The apparatuses, notwithstanding, are relatively large and expensive and require for their operation specially trained personnel in hospitals with rooms equipped for this purpose.

In view of the fact that a further development of the purely physical dialysis devices probably can result only in marginal improvements, development has recently turned in new directions. By combining the dialysis with various kinds of chemical activity, one has succeeded in improving the dialysis result and at the same time diminishing the dimensions of the dialysis devices. Moreover, the medical application range of the dialysis apparatus was widened beyond the dialysis at kidney failure. Among known devices, the chemical activity is assigned mainly to the dialysate part or, in some cases, to an ultrafiltrate, which subsequent to chemical treatment is returned to the patient's blood circulation.

By a continuous chemical purification of the dialysate the amount of dialysate can be reduced to a few liters and thereby renders it possible to design dialysis devices with considerably smaller dimensions than previously. The purification of the dialysate takes place, in principle, as follows: Urea transferred from the blood to the dialysate is degraded selectively by the enzyme urease in a free state to ammonium carbonate whereafter ammonium ions and other undesirable constituents separated from the blood are caught by adsorbents. The adsorbents usually are specific ones and have been preconditioned by known methods so as to catch the undesirable constituents, while the constituents desirable for the dialysate, e.g. chloride ions, remain in the dialysate. Known adsorbents are anionic and cationic exchange resins, zirconium phosphate, zirconium oxide and activated carbon.

The widened medical application range is related to such a form of enzyme therapy, the object of which is to selectively remove undesirable proteins from the blood for therapeutical purposes, for example, to degrade asparagine by means of L-asparaginase, as this was found to have a therapeutical effect on certain forms of cancer. Thereby, not only is kidney failure made accessible to treatment by a dialysis apparatus, but also, in principle, all pathological conditions, in which a therapeutical effect can be achieved by separating from the blood at least one undesirable constituent by means of a dialysis membrane, whereafter this constituent is selectively degraded on the dialysate side by an enzyme. Certain enzymes have a toxic effect and this is the reason why enzymes are not used in contact with the blood in such apparatus.

As examples, of known dialysis devices combined with chemical activity the following U.S. patent specifications can be referred to: According to the U.S. Pat. No. 3,608,729, to Haselden, it is known to purify a noncirculating dialysate by means of adsrobents, which are packed into pockets formed by a profiled dialysis membrane. As an adsorbent, there is used an ionic exchange resin, possibly in combination with activated carbon and with an enzyme in a free state, for example, urease to degrade urea. A vibrator is proposed to facilitate the transport of the constituents to be separated from the dialysate to the adsorbent.

U.S. Pat. No. 3,617,545, to Dubois, shows an electrodialyzer for the purification of dialysate and, alternatively, an ultrafiltrate (blood plasma), which contains constituents having molecular weights up to about 70,000, in several steps, comprising demineralization, degradation of urea by means of urease, cation exchange for adsorption of ammonium ions, remineralization, adsorption of uric acid and creatinine with activated carbon and adsorption of sulphate and phosphate ions by means of an anion exchanger.

U.S. Pat. No. 3,619,423, to Galletti et al., shows a cascade dialysis apparatus for the purification of blood, in which apparatus a dialysis section and an ultrafilter utilize one and the same recirculating dialysate and each contains a dialysis membrane, the pores of which permit substances with molecular weights up to about 10,000 to pass. An undesirable constituent in the blood which can pass through the membrane of the dialysis section into the dialysate, and which for a therapeutical purpose is desired to be selectively separated, is degraded with the corresponding enzyme in a free state, which is found in the dialysate. The constituents desirable for the blood are returned to the blood via the membrane of the ultrafilter which does not permit the passage of enzymes since these have molecular weights of about 100,000. The circulating dialysate is purified continuously by specific or non-specific adsorbents of a kind not stated in detail. The reduction of the asparagine content of the blood by means of L-asparaginase is mentioned as an example of chemotherapy of cancer. U.S. Pat. No. 3,669,878, to Marantz et al., shows a dialysate purification device for a conventional dialysis apparatus. The purification device, which is designed as a column traversed by the dialysate, is connected in series to the circuit of the dialysate. The column is filled with an inorganic adsorbent, such as zirconium phosphate, on which urease is adsorbed. The urease degrades, enzymatically, urea to ammonium carbonate. The zirconium phosphate acts as an ion exchanger and adsorbs the ammonium ions, whereas the sodium ions, which were adsorbed on the zirconium phosphate, are released according to a reaction formula which is shown hereinafter. The sodium ions are not harmful since they normally exist in great amounts in the dialysate.

In spite of the additional improvements obtained by the introduction of chemical activity in combination with dialysis, dialysis apparatuses for hemodialysis still are relatively large, expensive, technically complicated and are neither suitable nor possible for use at home. A further disadvantage of known apparatuses is that the pore size of the dialysis membranes must be limited to the passage of substances having molecular weights of up to 2500-3000, is order not to lose in the dialysate too great a number of constituents with a low molecular weight which are desirable for the blood. When, however, the afore-described method with an ultrafilter is used, the pore size can be increased to exemplified molecular weights of between 10,000-70,000. Alternatively, in a conventional dialysis apparatus with filters having larger pores, it is possible to balance the increased loss of desirable constituents in the blood by adding an excess of these constituents to the dialysate. Both of said alternatives result primarily in higher dialysis costs. When an ultrafilter is introduced, the apparatus increases in size and becomes more expensive and more complicated. To add the desirable constituents, for example, water soluble proteins, to a relatively great amount of dialysate, is uneconomical. There is evidence of the fact that impurities are found in the blood which have an incompletely known composition and molecular weights of between 10,000-15,000. According to an ever widely spread opinion in the large kidney clinics, a better dialysis result would probably be achieved, if these impurities could also be removed. Besides, an increase in pore size would facilitate the passage through the dialysis membrane and thereby shorten the time necessary for dialysis. A further disadvantage of known devices for hemodialysis is that the utilization of enzymes in order to selectively separate undesirable constituents from the blood for therapeutical purposes is restricted to the dialysate side. This restriction has its basis in the fact that several enzymes in a free state have an antigenic or other toxic effect on the blood, for which reason a direct contact between blood and enzyme has been avoided, because no safe method for insolubilizing the enzymes with maintained chemical activity was known. Several of the constituents to be selectively separated have relatively high molecular weights and, therefore, pass slowly through the pores of the dialysis membrane, so that the separation of the dialysate side takes more time than it would require with a direct contact between blood and enzyme. Therefore, it is desirable in hemodialysis to be able to use enzymes in contact with the blood without risk.

A remarkable development work has resulted in a better, simpler and cheaper hemodialysis, but the known dialysis apparatuses with associated peripheral equipment still require much space and are both expensive and complicated. Simultaneously, there is a demand partly to improve the dialysis result and partly to widen the application range in chemotherapy. It is a matter of great interest, particularly with respect to dialysis in kidney failure, to develop a simple, cheap, easy-to-service dialysis apparatus with good dialysis properties, which apparatus would render it possible to increase the number of dialysis treatments in hospitals at maintained reasonably low costs and also in suitable cases to perform the dialysis at home.

It is an object of the present invention to overcome the aforedescribed and other disadvantages involved with known dialysis apparatuses, specially so-called artificial kidneys.

Another object of the present invention is to produce a dialysis apparatus in the form of a compact, complete, easily operated and cheap unit, which in suitable cases also can be used for home dialysis.

Still another object of the present invention is to bring about an improvement in the dialysis result.

A further object of the present invention is to be able to perform a hemodialysis in a shorter time than is possible with known apparatus.

Another object of the present invention is to also separate from the blood impurities with a high molecular weight, up to 10,000-15,000 whose structures are not completely known.

Still another object of the present invention is to combine dialysis through a semipermeable membrane with chemical activity on the dialysate side of the membrane in order to purify the dialysate.

A further object of the present invention is to combine dialysis through a semipermeable membrane with chemical activity on the blood side of the membrane in order to selectively and without toxic side-effects affect both the liquid phase of the blood and the blood cells for achieving a therapeutical effect under different pathological conditions.

A further object of the present invention is to design the dialysis apparatus so that it involves the smallest possible risk of spreading inoculation hepatitis.

Another object of the present invention is to prevent the coagulation of blood in the dialysis apparatus.

The advantages involved with the aforesaid objects have been achieved with a dialysis apparatus according to the present invention, partly by applying some prior art methods with a good combinational effect, which were known individually or in combination with dialysis and, respectively, biochemistry, and partly by providing the apparatus according to the present invention with a new and improved design. The factors contributing to the said good combinational effect are as follows:

1. The apparatus is provided with a dialysis membrane, the pore size of which permits the passage of constituents with molecular weights up to between 10,000 and 15,000. Such membranes can be manufactured by known methods (Craig, L. C. and Koningsberg, W. O., Phys. Chem., 65, 166, 1961) of, for example, cellulose base, partially saponified cellulose acetate, copolymers of vinyl acetate and vinyl alcohol, homo- or copolymers of polymethyl-, hydroxypropyl-, glycerol- or glycidil methacrylate and of copolymers of acrylonitrile. Particularly suitable are those membrane materials, which are characterized by a certain hydrophily and the surface of which by hydrolysis or other known methods receives an increased amount of hydroxyl groups, which facilitates the method described below in item 2 for rendering the surface selectively chemically active. The increase of pore size in the dialysis of blood from molecular weights of 2500–3000, as they are possible with known apparatuses, to 10000–15000 provides two advantages, viz. the possibility of separating from the blood the aforementioned impurities, which are incompletely known as to their composition and which have molecular weights from about 3,000 up to 10,000–15,000, and a shorter time required for the dialysis due to said increased pore size. Also, the simultaneously arising disadvantage that several constituents which are important and desirable for the blood and have molecular weights below 10,000–15,000 can pass through the pores, is eliminated by the factors described in items 3 and 4.

As examples of constituents, which have molecular weights of up to about 3,000 and which are separated by known technique, can be mentioned ionizable or non-ionizable acids dissolved in water, salts, urea, creatinine and sugar types. For those cases, in which it is considered sufficient to separate these substances and to refrain from the separation of the aforesaid impurities with molecular weights from about 3,000 up to 10,000–15,000, the apparatus according to the invention can be provided with a dialysis membrane having the pore size for a substance having a maximum molecular weight of 3,000 and yet obtain substantial advantages over known dialysis apparatuses.

2. The surface of the dialysis membrane has been made selectively chemically active by insolubilizing at least one chemically active substance on that side where the chemical activity is of interest. The active substances are proteins such as enzymes and antibiotics, which by covalent bonds are very highly insolubilized at the surface of the dialysis membrane. The method results both in a substantially longer active life of the substance in question and permits the use of active substances with antigen or other toxic effect, when such use is motivated for therapeutical reasons, in direct contrast with blood, because none of or only negligible amounts of the substance pass out in a free state into the blood. These properties have been confirmed by clinical tests carried out for more than 2 years. The tests utilized an extracorporeal device intended for enzyme therapy and which is described in Arzneimittel-Forschung (Drug Research) 21, 1671–1675 (1971). In said tests it was found, that the enzyme L-asparaginase, which was insolubilized on a matrix in contact with blood in order to lower the asparagine content in the blood, has no appreciable antigen effect or other side effect on, for example, thrombocytis or by developing allergic conditions.

Insolubilization of the selectively chemically active substance on the dialysis membrane surface facing toward the dialysate is of interest when impurities originating from the blood are to be removed from the dialysate in order to keep the composition of the dialysate constant. One can, for example, by using the enzyme urease, degrade urea to ammonium carbonate, which in its turn is adsorbed as explained below in item 3. According to the aforesaid, this reaction can also be placed on the blood side of the dialysis membrane, but since urea passes through the pores of the dialysis membrane without difficulty, there is no reason for unnecessarily placing the enzyme reaction on the blood side. When, however, it is desired to selectively separate a substance from the blood such as, for example, a protein with a molecular weight so high that it cannot at all or only with difficulty pass through the pores of the dialysis membrane, then the enzyme must be insolubilized on the blood side. The intimate contact between the blood and the chemically active surface is favourable for the reaction. The degradation products have a low molecular weight and pass easily through the dialysis membrane to the dialysate where they are adsorbed as described in item 3. The dialysis, therefore, proceeds rapidly.

A group of substances which are considered responsible for some toxic symptoms in kidney failure, such as disturbances in the nervous system, are indole substances, indole, indican and other tryptophane derivatives. The selective chemical activity is placed on the blood side of the dialysis membrane and other constituents are removed from the blood by enzymatic degradation.

Mycosis infections are a serious disease condition, access to which heretofore was difficult for effective treatment. Antibiotics are known which are highly effective against these fungus types. Unfortunately, they cannot be used in free form because they are also highly toxic. With a known method, however, an antibiotic can be insolubilized on a dialysis membrane of the aforesaid kind, whereby the antibiotic with maintained chemical activity is insolubilized on the dialysis membrane by covalent bonds. The bonding to the dialysis membrane is very strong and, therefore, no antibiotic occurs in free form. According to the present invention, by the insolubilization of a suitable antibiotic on the blood side of the dialysis membrane, an effective and riskless form of therapy of mycosis infections is obtained.

Enzymes, antibiotics and substances having a similar chemical nature can be insolubilized on a carrier consisting of anyone of the materials preferred in item 1 for the dialysis membrane by means of any known insolubilization method, for example the silanizing method or the cyanobromine method. The principle is described in detail a.o. in Weetall, H. H. and Weliky, N., Nature 204, 896, 1964, Porath, J., Axen, R. and Ernback, S., Nature 215, 1491, 1967 and Mosbach, K., Acta Chem. Scand., 24, 2084, 1970.

3. The dialysate is purified continuously from the impurities passing through the dialysis membrane by means of adsorbents, which are known in other connections and have a physical and chemical adsorbing effect and which, where possible, have been made selective for the impurities in question by known methods. As examples of adsorbents of the kind concerned can be mentioned activated carbon and inorganic ion exchangers, zirconium phosphate and/or zirconium oxide specially preconditioned for this purpose. In order to improve the effectiveness, small cellulose balls are preferably used as carriers for the adsorbents. The adsorbents are arranged in the circulation system of the dialysate in the manner described below.

In order to maintain the dialysate and the adsorbent moving relative to one another and thereby to facilitate the transport of those constituents in the dialysate which are to be adsorbed, the dialysis part of the apparatus is preferably provided with a vibrator, which may be small, simple and of an optional type, but is preferably electrically operated. A suitable oscillation frequency is about 5–10 cycles per second. The composition of the dialysate can, by means of the adsorbents, be kept practically constant during a dialysis treatment. The adsorbents and the apparatus details, in which they are disposed, are intended to be discarded and replaced by new ones after each treatment. Therefore, it is advantageous that only a relatively small amount of an expensive substance, such as a zirconium preparation, be required for a treatment. Moreover, it is possible to regenerate the zirconium preparation according to known methods when such regeneration is economically profitable. The greatest advantage of being able to maintain the composition of the dialysate constant is that it is possible without deterioration of the dialysis result, to reduce the amount of necessary dialysate from 250–1000 liters as required by known techniques to a few liters, viz. according to calculations and practical tests with an apparatus for hemodialysis to 3–5 liters. This has become partly possible in that the apparatus according to the invention could be given the desired small dimensions and the desired simple design, and partly in that the constituents which, as mentioned in item 1, are important for the blood and have a low molecular weight, and which are lost through the dialysis membrane, can be added to the dialysate at reasonable costs, whereby said loss is balanced. It is, further, possible to add, to the dialysate, substances having molecular weights of about 8–9000, for example a hormone, e.g. thyreoglobulin or a growth hormone for children.

The apparatus is provided with means in the form of at least one small and simple drop dosimeter disposed on the dialysate supply container for continuously adding to the dialysate the substances which are important for the blood as mentioned in items 1 and 3.

The combination effect reported above in items 1–4 has rendered it possible to design the apparatus according to the invention along lines which are entirely novel in several respects and provide essential advantages. The basic layout of the apparatus and the resulting advantages are briefly described in the following:

The desire of obtaining a dialyzer in the form of a small, compact and easy-to-service unit has been satisfied when a container for the dialysate simultaneously serves as a stand for other components, which to the greatest possible extent are simplified and miniaturized and which are limited in number to what is absolutely necessary from an operation and safety point of view. The unit thus designed is a lightweight, transportable apparatus which, inclusive of the dialysate, has a weight of only about 5–7 kg and for its operation may be connected only to a normal mains socket or, alternatively, an electric battery mounted on the apparatus.

The principle which requires that, if possible, all medical equipment which involves the risk of spreading inoculation hepatitis to patients and medical staff members, should be disposable, is applied consistently. Only the dialysate container with the control and operation components attached thereon is intended for repeated use. The remaining components, which directly or indirectly come into contact with the blood, as well as those carrying the adsorbents, are discarded after each treatment. A complete set of these latter components plus the necessary additives for the dialysate are, due to the small amounts and dimensions and the simple design, substantially cheaper in cost than corresponding components of known dialyzers. The structural material in the apparatus according to the invention, if not specified otherwise, can be selected among the materials, which have already been tested in connection with dialyzers, heart-lung machines and similar apparatuses. The disposable details preferably are made of plastic material.

The feature that the dialysis membrane is given the form of a flat hose, which together with an intermediate distance and support member in the form of a flexible strip with open structure is helically wound and located in a cylindric container, provides several advantages. The blood and, respectively, dialysate can easily be led to and from the container by means of two connections per circuit which are located on the shell surface of the container, or its cover and, respectively, its bottom. The circuits preferably are connected in counter-flow for rendering maximum dialysis effect. It will become apparent from the following embodiment, that the components disposed in and on the cylindric container can be mounted in a simple manner with satisfactory sealing and without risk of leakage between the two circuits for the blood and, respectively, dialysate. As a practical example of the small dimensions of the apparatus can be mentioned that, if the dialysis membrane is given a total active surface of 0.99 $m^2$, the length is 2.08 m and the distance between two adjacent membrane layers is 0.35 mm, then the total volume is 0.35 liter, about half of it being blood. The small amount of blood in the apparatus, about 175–200 ml, is an advantage, because no blood from a blood bank need be used for priming the system before its use nor must a blood substitute, for example Rheo-macrodex solution, be supplied to the patient. Blood remaining in the apparatus after the dialysis can easily be returned to the patient by filling an adjusted amount of a liquid neutral to the blood through the blood supply hose. The blood loss arising from a dialysis treatment can thereby be held negligibly small. The blood and dialysate run in a laminar flow on both sides of the dialysis membrane, and the small distance, about 0.35 mm, between contiguous membranes implies a good contact between the liquids and the membrane, which facilitates the dialysis. Also a contributing factor is the vibrator mentioned in item 3. With the dimensions indicated above, the flow resistance of the blood will not exceed the difference in pressure which normally exists between an artery and a vein and more than the necessary amount for blood about 200 ml/min, will be able to flow through the apparatus. The need for a blood pump is thereby eliminated in most cases.

For circulating the small amount of dialysate which is concerned here, a small simple optional type pump with an associated electro-motor is sufficient.

The adsorbents are provided both by being pressed into the open structure of the aforesaid distance and supporting member and in a separate purifying cartridge in the return line of the dialysate. Both of these components with adsorbents are discarded after completed dialysis. The adsorbents are provided in two places so that the purifying effect will be better and the safety greater. The purifying cartridge in the return line can, if this exceptionally should be necessary, be exchanged whilst the dialysis is going on.

In order, during the proceeding dialysis, to supply to the dialysate adjusted amounts of the constituents important for the blood and having a molecular weight passing through the dialysis membrane, the supply container for the dialysis is provided with at least one, preferably several threaded pipe sockets, their mouths being covered with exchangeable elastic membranes. A drop dosimeter which is known per se, and which is formed as a bottle having an externally threaded neck and a canule-shaped outlet, is connected to the pipe socket. The canule is pierced through the elastic membrane, and the bottle is threaded into the pipe socket. The liquid additives can then be metered in a manner known per se.

The apparatus can also be provided with a safety device, which in the dialysis of blood emits an acoustic and/or optical signal when blood passes out into the dialysate or when the patient is subjected to hemolysis, since in both cases the dialysis must be interrupted. Said safety device comprises a small and simple spectrometer, which is disposed about or in the return line of the dialysate with the filter of which being so chosen as to indicate an absorption typical of hemoglobin. There is connected to said spectrometer a conventional electronic alarm circuit which includes a buzzer and/or a warning lamp.

In order to prevent the cooling of the blood, the apparatus according to the invention is provided with a thermostat-controlled heating device, which preferably is electric and disposed in the supply container for the dialysate. The heating device may be provided with external insulation for the supply container by means of, for example, expanded polystyrene, glass wood or any other suitable insulation material.

Furthermore, during the dialysis of blood, all surfaces coming into contact with the blood consist of known non-thrombogenous materials or are made non-thrombogenic in a known manner by being heparin bonded at the surfaces.

As an example of the efficiency of the apparatus, the result of four tests with an urea solution are reported below, at which the urea concentration was set to high values, which are observed in the blood during kidney insufficiency, i.e. 350 mg/100 ml.

During the tests an apparatus according to the invention was used, the dimensions of which were reduced to laboratory test scale and had the following data:

The dialysis membrane was a cellulose base with an active surface of 0.3 $m^2$ on the flat helically wound hose of 3.50 m length. The distance between contiguous membranes was 0.5 m. Urease was insolubilized on the membrane surface facing toward the dialysate (=outer system) with an urease solution containing 100 IE/ml in a $10^{-2}$ M buffer solution, pH 7.3, according to a known method of Weetall and Weliky. The inner system contained 500 ml urea solution, 350 mg/100 ml $10^{-2}$ M buffer, pH 7.4, which circulated with 150 ml/min. The outer system contained 1000 ml $10^{-2}$ M buffer, pH 7.4, which circulated in a counter-flow with 380 ml/min. The apparatus, in order to obtain "pure" test values, did not contain adsorbents. The tests were carried out at room temperature. [$NH_4+$] was measured with a cation-electrode, and with an ammonium probe. The [$NH_4+$]-content was measured in the inner and outer solution during a dialysis time of 4 h. The urea amount corresponding to the [$NH_4+$]-concentration was calculated in both solutions and summed up whereafter the mean values for the four tests were calculated. The urea concentration had after 4 h decreased from 350 to 180 mg/100 ml. The individual tests showed a spread about the mean value of ±18 mg/100 ml.

If in the aforesaid test series an adsorbent, preconditioned zirconium phosphate, would have been provided in the outer system, which would have been the case in dialysis treatment of blood in vivo, the adsorbent would have taken up the ammonium supplied at the dialysis. The dialysis thereby would have proceeded still faster at the same time as ammonium was transported from the inner to the outer system.

Figure 2:
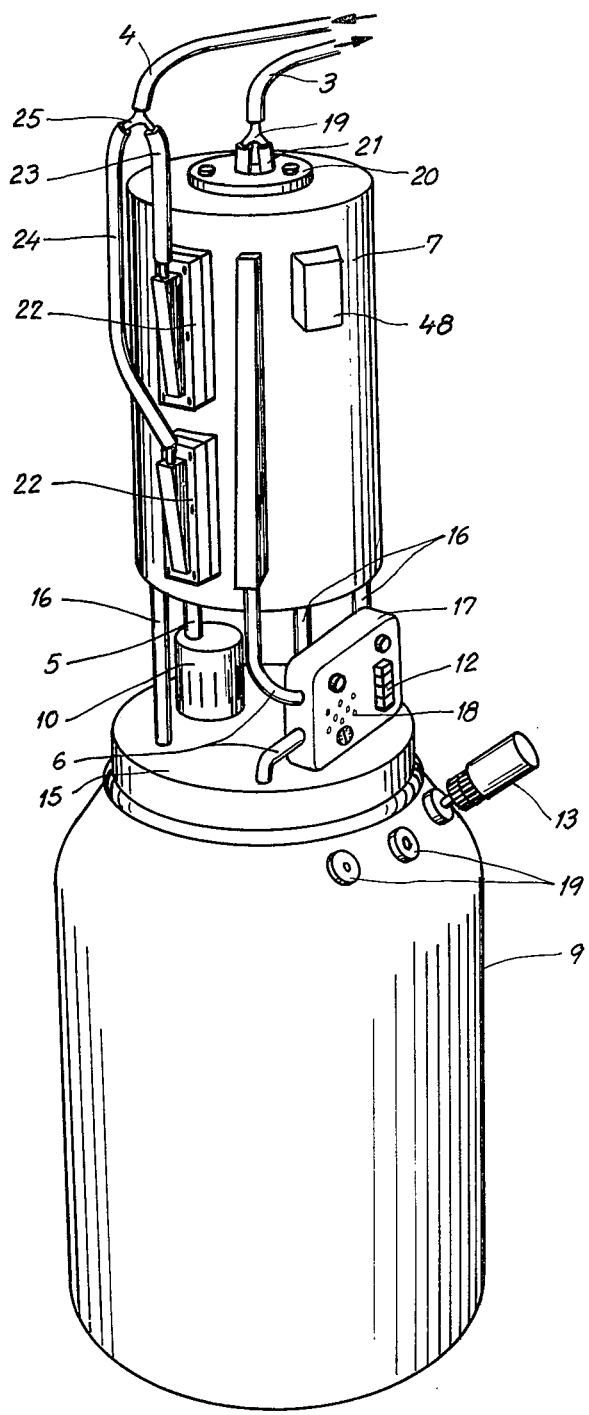
Figure 3:
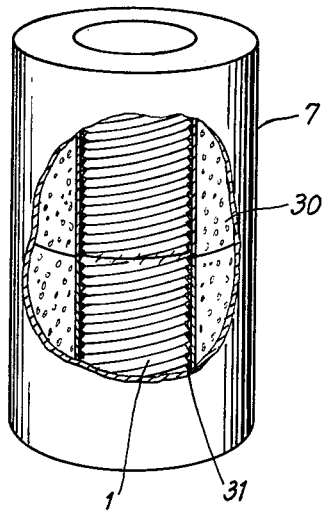
Figure 4:
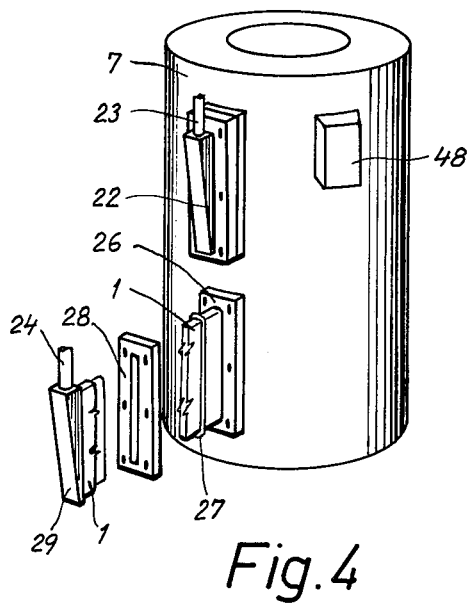
Figure 5:
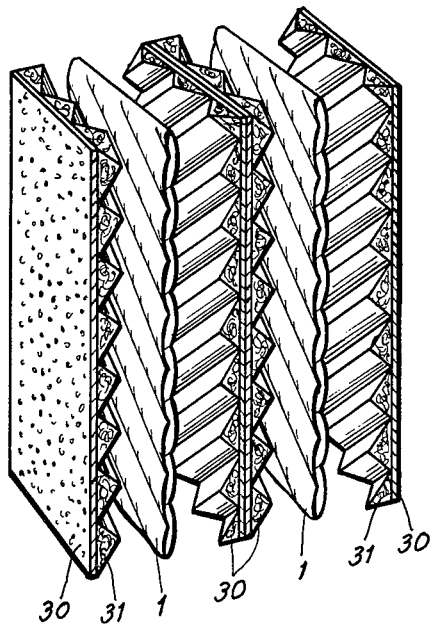
Figure 6:
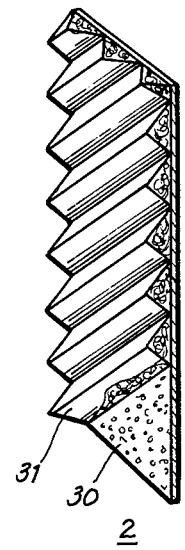
Figure 11:
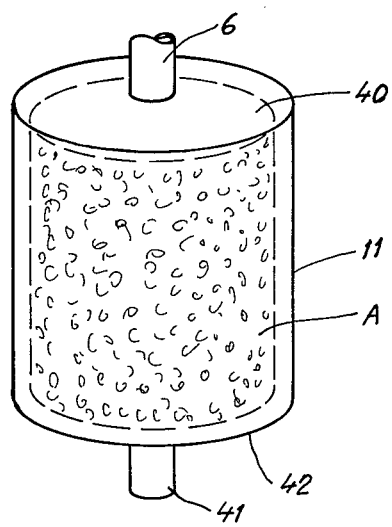
Figure 12:
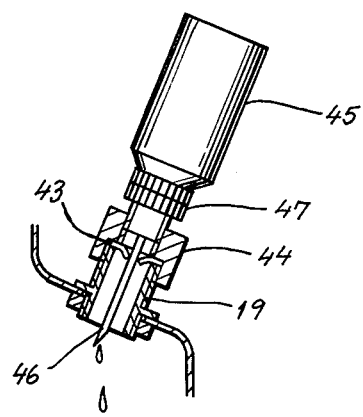

A preferred embodiment of the invention is described in greater detail in the following with reference to the accompanying drawings, in which FIG. 1 shows a basic layout of the invention, FIG. 2 is a perspective view of a dialysis apparatus according to the invention, FIG. 3 is a perspective view of a dialysis cylinder partially cut open, FIG. 4 is a perspective view of the dialysis cylinder according to FIG. 3, with connections for blood supply, one connection being shown pulled apart, FIG. 5 is a perspective view of a section of a dialysis hose with associated distance member, FIG. 6 is a perspective view of a spread portion of the distance member according to FIG. 5, its carrying part being partially exposed, FIG. 7 is a perspective view of an alternative embodiment of a distance member, FIG. 8 is a horizontal view of a cross-section through mounted distance members according to FIG. 7, FIGS. 9 and 10 are sectional and, respectively, perspective views of a spectrometer, FIG. 11 is a perspective view of a purifying cartridge with adsorbents, and FIG. 12 is a longitudinal section through a drop dosimeter.

In all Figures, one and the same detail is designated by the same reference character.

The basic layout of the apparatus is apparent from FIG. 1. A dialysis membrane in the form of a flat hose, together with an intermediate spacer or distance member 2, is helically wound and disposed on a cylindric dialysis container 7 as shown in FIG. 2. The interior of the hose-shaped dialysis membrane forms an active part of an inner circuit for the liquid to be dialysed. The space formed by the distance member 2 between the turns of the membrane 1 constitutes an active part of an outer circuit for the dialysate 8. The two circuits are connected in counter-flow relationship. The inner circuit is provided with a supply hose 3 and an outlet hose 4, which in the dialysis of blood are connected to an artery and, respectively, a vein. A dialysate container 9 is provided in the outer circuit for the dialysate 8 and has a pump 10, which pumps the dialysate 8 through a supply hose 5 to the dialysis part of the outer circuit, from which the dialysate is returned through a return hose 6, which is connected to a purification cartridge 11 immersed into the dialysate container 9. The return hose 6 extends through a hole in the beam path for a spectrometer 12 which is provided in an electronic circuit of a known kind (not shown) which includes an optic and/or acoustic alarm device so as to give an alarm if blood or hemoglobin appears in the dialysate 8. A thermostat-controlled heating device 14 is provided in the dialysate container 14 to maintain the dialysate at body temperature. An exchangeable drop dosimeter 13 of any known kind is arranged on the dialysate container 9 and renders possible a continuous supply of additives to the dialysate. On the surface included in the inner circuit of the dialysis membrane 1, enzyme, antibiotic or another selectively active substance depending on the therapeutic activity desired in the individual case is insolubilized.

As seen in FIG. 1 and designated by E these substances can in applicable cases be insolubilized alternatively on the dialysis membrane surface facing toward the dialysate 8. The material and pore size of the dialysis membrane are as hereinbefore described. The distance member 2, which is described in the following, has an open structure, into which the adsorbent designated by A is impressed. Also the purification cartridge 11 contains adsorbent of the aforesaid kind.

A small electric vibrator 48 is mounted on the outside of the dialysate container 7, as seen in FIG. 2, in order to intensify the liquid flow about the dialysis membrane 1 and, respectively, adsorbent A and thereby to accelerate the dialysis as well as to prevent the blood from coagulating where the flow velocity is low.

FIG. 2 illustrates how the apparatus components shown in FIG. 1 can be arranged in a suitable manner. The Figure shows the lower portion of the dialysate container 9, above the cover 15 of which the dialysis container 7 is mounted on supports 16. The pump 10 is mounted directly on the cover 15, and there is further mounted an instrument box 17, which includes the spectrometer 12 with an associated alarm device, for example a buzzer 18 and necessary control means. The drop dosimeter 13 is threaded into one of the pipe sockets 19 which is provided for this purpose at the upper portion of the dialysate container 9.

In view of the difficulty in procuring a flat dialysis hose of sufficient width, the dialysis container 7, FIGS. 2–4, contains two helical units connected in parallel which consist of the dialysis membrane 1 and the distance member 2 of the aforesaid kind described in relation to FIG. 1. For the inner circuit, i.e. the mouths of the hose-shaped dialyses membranes 1, separate connections to the supply and return hoses 3 and 4, respectively, are provided. The supply takes place via a central distribution means, which is substantially concealed in FIG. 2, the outer part of which consists of a supply socket 20 which is provided on the upper surface of the dialysis container 7 with two distribution hoses 21 and one branch pipe 19, to which the supply hose 3 is connected. The concealed part of the distribution means is in principle identical with a corresponding collecting means provided on the shell surface of the dialysis container 7. The collecting means consists of two connections 22, as seen in FIGS. 2 and 4, fastened on the shell surface of the dialysis container 7 by means of hoses 23, 24 connected to a branch pipe 25, which in its turn is connected to the return hose 4. Each connection comprises a base 28, as seen in FIG. 4, a gasket 27, a washer 28, a hose base 29 clamped in the washer 28 for the hose-shaped dialysis membrane 1 and the return hose 23 and, respectively, 24.

FIG. 3 shows in the sectional portion how the two sets with the dialysis membrane 1 and distance member 2 are disposed upon one another. The distance member 2, as seen in FIG. 6, consists of a base portion 30, which is provided with fine through holes and serves as a carrier for an open structure in the form of ridges 31 fastened thereon and forming an oblique angle (about 45°) with the longitudinal direction of the distance member 2. The oblique-angled ridges 31, upon the helical winding of the distance member together with the dialysis membrane 1 form, in adjacent turns, angles with each other. The points of intersection between ridges 31 located against each other form thereby a chequered pattern of supporting points for the dialysis membrane 1, FIG. 5. This arrangement provides both the desired distance between contiguous turns of the dialysis membrane 1, and in a simple manner uniformly distributed supporting points over the entire surface of the dialysis membrane. As mentioned before, the open structure of the ridges 31 is filled with the adsorbent or adsorbents used and designated in FIG. 1 by A.

The distance member can, alternatively, be designed as a plastic-bonded, thin, flexible I-shaped beam 32 moulded of a fibrous material, FIGS. 7 and 8. When the distance member 32 is wound to helical shape, a channel 33 is formed between two contiguous turns, which channel encloses the dialysis membrane 1. The open fibrous structure of the distance member 32 is filled with the adsorbent A.

The spectrometer 12, as seen in FIGS. 1, 9 and 10, is a miniature spectrometer of simple design. It consists of a parallelepipedic frame 34, which is provided with a through hole 35 for a lamp 36, a filter 37 and a photoelectric cell 38. A second hole perpendicular to the hole 35 for the return hose 6 is so arranged that the return hose 6 of transparent material will intersect the beam path between the lamp 36 and the photoelectric cell 38. The filter 37 is so chosen that its absorption is typical of hemoglobin. When the absorption exceeds a certain pre-set value determined for safety reasons, the electronic circuit which is known per se and comprises the spectrometer 12, is actuated. The buzzer 18 is thereby energized and emits a warning signal.

The purification cartridge 11, as seen in FIGS. 1 and 11, is formed as a cylindric container, which contains the adsorbent A in a suitable state, for example, granular. The cartridge 11 is suspended vertically immersed into the dialysate 8 in the return hose 6, which is connected to a hose base provided on the upper end wall 40 of the cylindric container. On the opposed end wall 42 forming the purification cartridge 11, a short discharge pipe 41 is provided. In order to prevent the adsorbent from being flushed out, the end wall 42 is covered on the inside with glass wool, fine-meshed cloth 49 or the like, as seen in FIG. 1. Impurities in the dialysate 8 which were not adsorbed by the adsorbent in the distance member 2, are adsorbed in the purification cartridge 11, whereby the composition of the dialysate 8 is maintained constant as the dialysis proceeds. The adsorbent in the purification cartridge 11 can be recovered and regenerated, if this is deemed profitable.

The drop dosimeter 13, as seen in FIGS. 1, 2 and 12, is located on the upper portion of the dialysate container 9 and comprises at least one, but preferably three to four pipe sockets 19 with external threads. A membrane 43 of rubber or another elastic material covers the mouth of the pipe socket 19 and is retained by a nut 44. A bottle 45 containing the additive to be metered is provided with an outwardly threaded neck and a canule-shaped discharge pipe 46. This discharge pipe 46 is pierced through the membrane 43 whereafter the bottle 45 is threaded into the nut 44. By adjusting a valve (concealed in FIG. 12) by means of a valve nut 47, an adjusted amount of air is passed into the bottle 45, and thereby the additive is metered out through the discharge pipe 46. Several designs of devices operating after this principle for sterile metering of a liquid are known.

According to an alternative embodiment of the invention (not shown), the dialysis part of the apparatus is formed as a parallelepipedic dialysis container, which includes dialysis membranes and distance members of the aforesaid kind as a battery of flat elements, i.e. in a manner which is usual among known dialyzers.

I claim:

1. A dialysis apparatus comprising a dialysate container, cover means for said dialysate container, a dialysis container mounted on said cover means, said dialysis container having an inlet means and an outlet means, spectrometer means mounted on said cover means, a first fluid circuit means connecting said dialysis container and said dialysate container through said spectrometer means, said first fluid circuit including purification means in said dialysate container, a dialysis membrane for permitting passage of substances with molecular weights of up to between 10,000–15,000 removably mounted in said dialysis container and having a selectively chemically active therapeutic substance insolubilized on at least the surface facing the liquid to be dialyzed, pump means mounted on said cover means for pumping dialysate from said dialysate container to said dialysis container, a second fluid circuit means connecting said pump means with said dialysate container and said dialysis container, and at least one dosimeter means on said dialysate container for metering fluid into said dialysate container.

2. The dialysis apparatus of claim 1 including heating means in said dialysate container.

3. The dialysis apparatus of claim 1 including signal means in combination with said spectrometer means.

4. The dialysis apparatus of claim 1 wherein said membrane is in the form of a helically wound flat hose and said membrane is wound with a distance means.

5. The dialysis apparatus of claim 1 including vibrator means mounted on said dialysate container for intensifying the liquid flow about said membrane.

6. The dialysis apparatus of claim 1 wherein said purification means is an adsorption means.

7. The dialysis apparatus of claim 1 including distribution means for distributing the liquid about said membrane.

8. The dialysis apparatus of claim 1 including further purification means.

9. The dialysis apparatus of claim 1 wherein said chemically active therapeutic substance is selected from the group consisting of enzymers, antibiotics, antigens, antibodies and synthetic adsorbents.

10. A dialysis apparatus comprising a dialysate container, cover means for said dialysate container, a dialysis container mounted on said cover means, said dialysis container having an inlet means and an outlet means, spectrometer means mounted on said cover means, a first fluid circuit means connecting said dialysis container and said dialysate container through said spectrometer means, said first fluid circuit including purification means in said dialysate container, a dialysis membrane for permitting passage of substances with molecular weights up to 10,000–15,000 removably mounted in said dialysis container and having a selectively chemically active therapeutic substance selected from the group consisting of L-aspariginase, urease and an antibiotic insolubilized on at least the surface facing the liquid to be dialyzed for purifying liquid passing through said apparatus, pump means mounted on said cover means for pumping dialysate from said dialysate container to said dialysis container, a second fluid circuit means connecting said pump means with said dialysate container and said dialysis container, and at least one dosimeter means on said dialysate container for metering fluid into said dialysate container.

* * * * *